United States Patent [19]
Kuracina et al.

[11] Patent Number: 5,336,197
[45] Date of Patent: Aug. 9, 1994

[54] HARD COVER FOR PROTECTED INJECTION APPARATUS

[75] Inventors: Thomas C. Kuracina, Ojai; Randall E. Ohnemus; Craig W. Smith, both of Ventura, all of Calif.

[73] Assignee: InjectiMed, Inc., Ojai, Calif.

[21] Appl. No.: 111,162

[22] Filed: Aug. 24, 1993

Related U.S. Application Data

[62] Division of Ser. No. 850,681, Mar. 10, 1992, Pat. No. 5,254,099.

[51] Int. Cl.$^5$ .............................................. A61M 5/32
[52] U.S. Cl. ........................... 604/192; 604/263; 206/365
[58] Field of Search ............... 604/111, 192, 198, 263; 206/365, 366

[56] References Cited

U.S. PATENT DOCUMENTS

| | | | |
|---|---|---|---|
| 3,101,841 | 8/1963 | Baldwin | 206/365 |
| 3,149,717 | 9/1964 | Castelli | 206/365 |
| 3,329,146 | 7/1967 | Waldman | 604/192 |
| 3,333,682 | 8/1967 | Burke | 604/263 |
| 4,816,024 | 3/1989 | Sitar et al. | 604/263 |
| 4,878,902 | 11/1989 | Wanderer et al. | 604/263 |
| 5,163,915 | 11/1992 | Holleron | 604/263 |

FOREIGN PATENT DOCUMENTS

| | | | |
|---|---|---|---|
| 8910767 | 11/1989 | PCT Int'l Appl. | 604/263 |
| 0828050 | 2/1960 | United Kingdom | 604/263 |

*Primary Examiner*—John D. Yasko
*Assistant Examiner*—Anthony Gutowski
*Attorney, Agent, or Firm*—Donald A. Streck

[57] ABSTRACT

This invention is directed to covers for holding and protecting needles of medical devices prior to use. It includes covers for holding and protecting needles of medical devices in which the needles are, in turn, contained within a retractable protective sleeve. In such case, the needle and its protective sleeve are held within the cover by a wedging action of a base portion with the cover. The cover contains projections which grip the base so that the needle and its protective sleeve can be turned with the cover to twist them on and off of the medical device safely. Longitudinal vanes in the cover can be included to hold a spring and locking collar over the protective sleeve in a retracted state prior to use. A cap with a flat end and square shoulders is aligned with a flat side of the cover and the entirety closed with a frangible security strip to indicate any possible tampering prior to use.

4 Claims, 6 Drawing Sheets

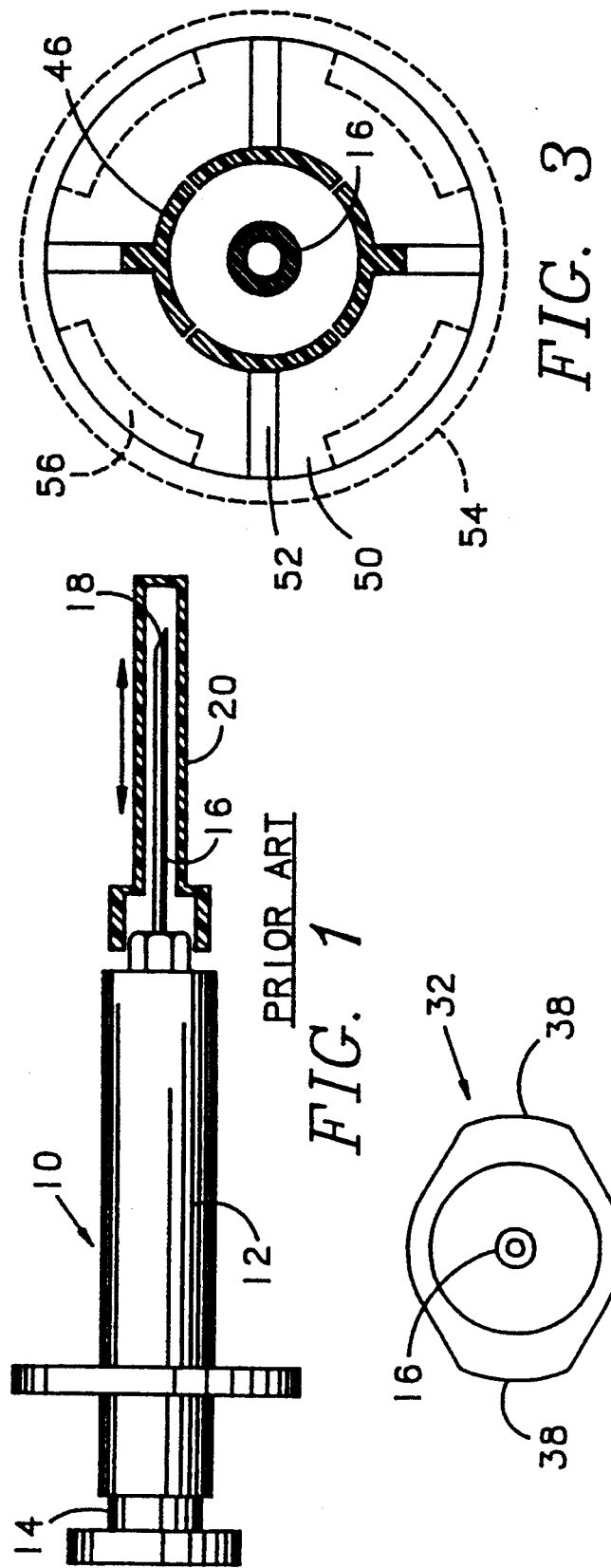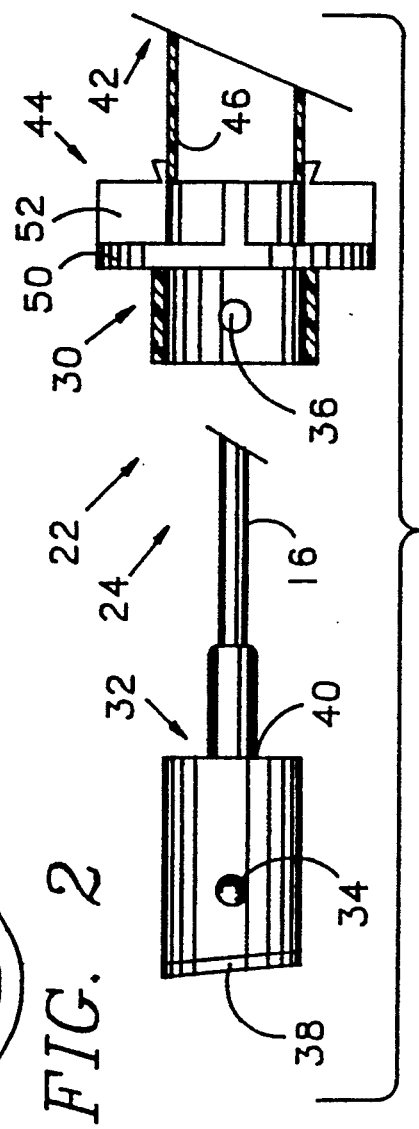

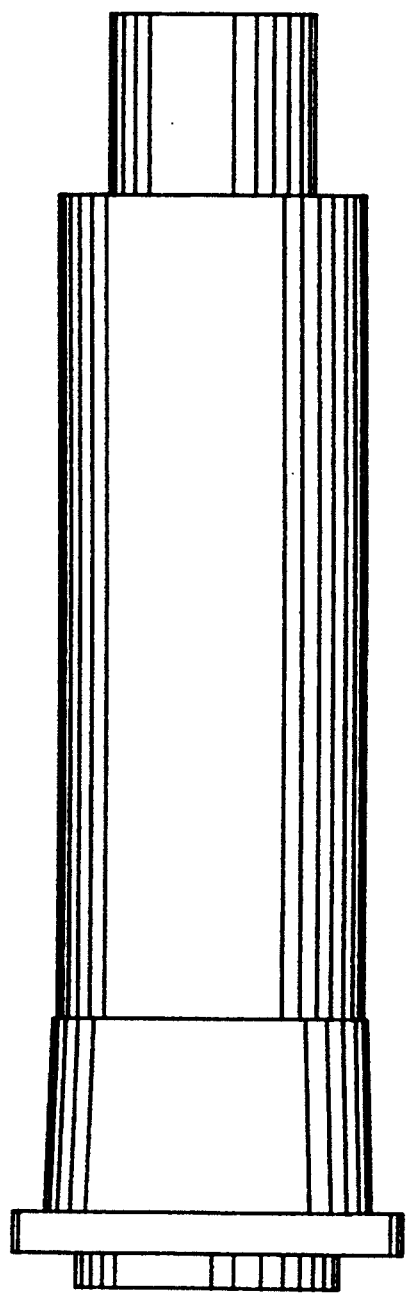
FIG. 7
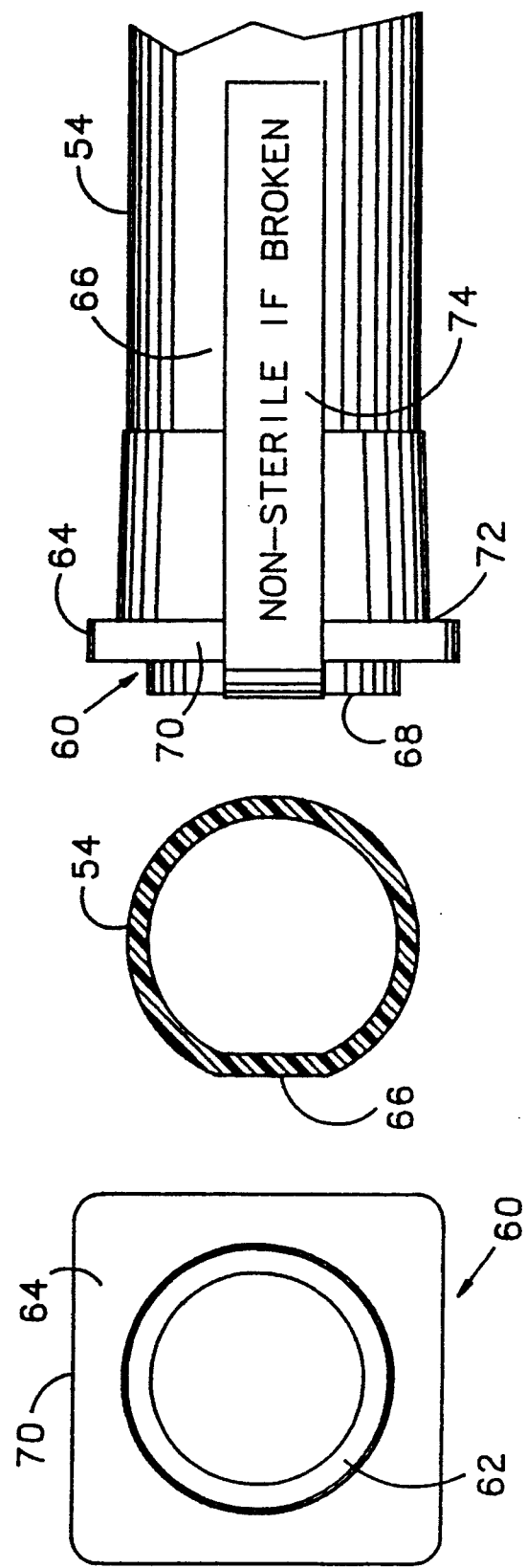
FIG. 10
FIG. 9
FIG. 8

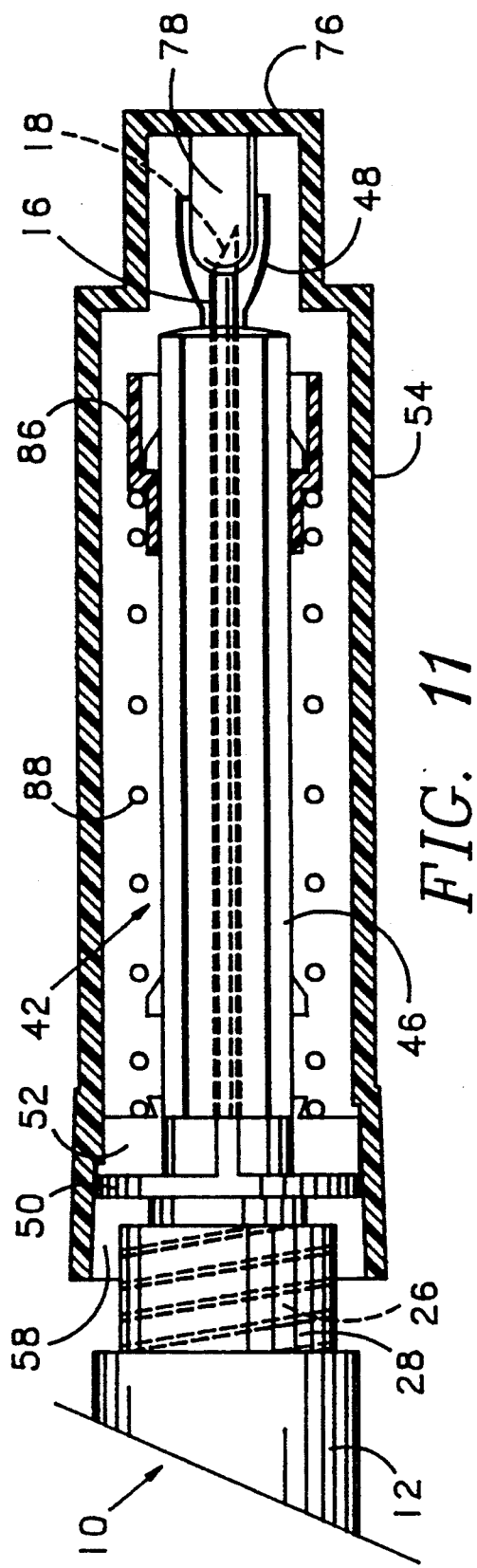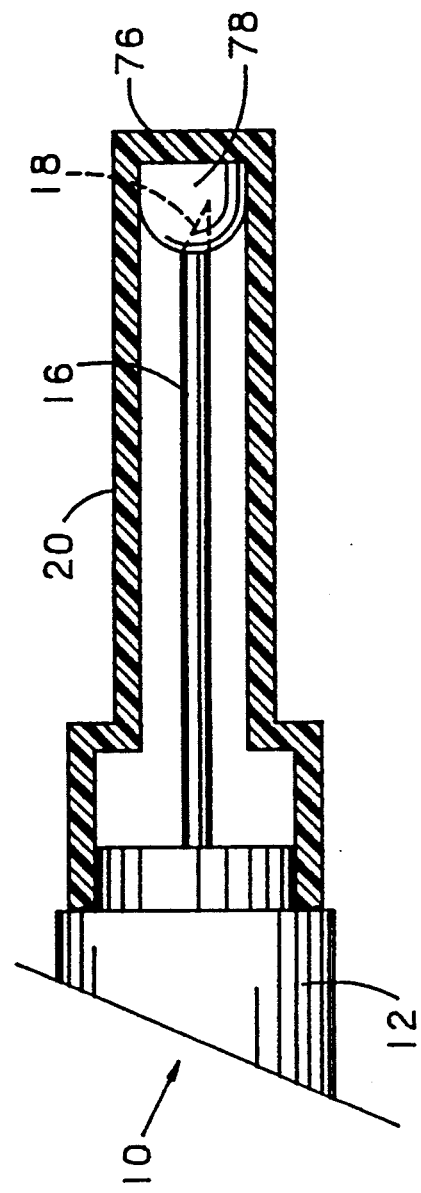
FIG. 11
FIG. 12

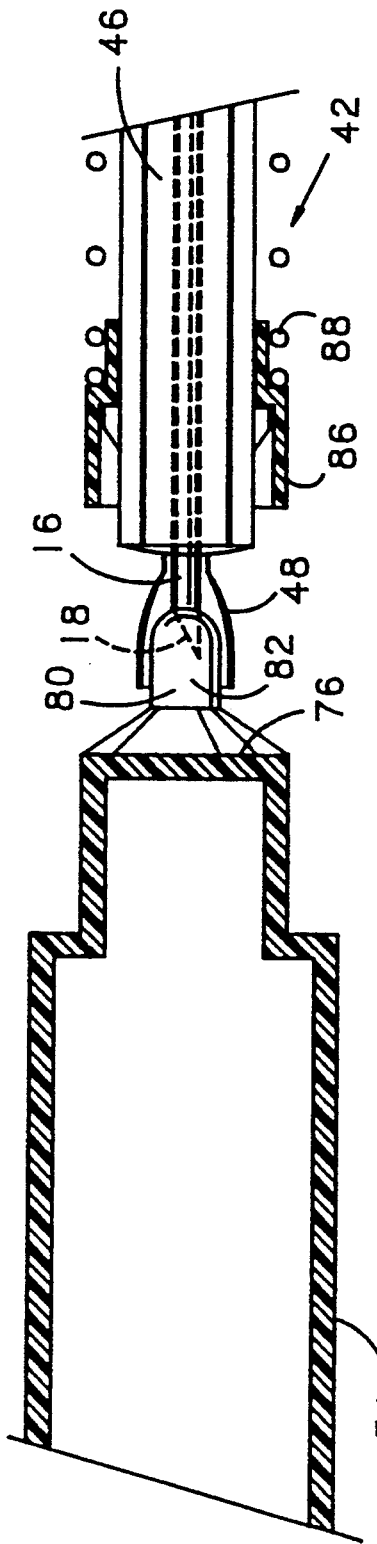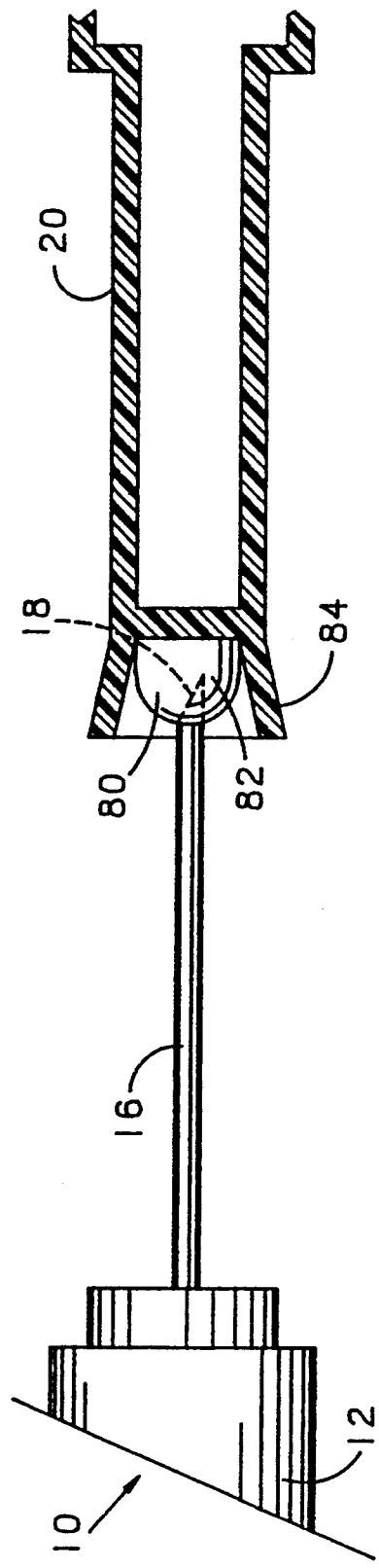

HARD COVER FOR PROTECTED INJECTION APPARATUS

This application is a division of application No. 07/850,681, filed Mar.10, 1992, now U.S. Pat. No. 5,254,099.

BACKGROUND OF THE INVENTION

This invention relates to medical devices for injecting living bodies and, more particularly, to covers for holding and protecting needles of medical devices prior to use.

In U.S. Pat. No. 4,998,922 by Thomas C. Kuracina entitled SAFETY SYRINGE CAP MINIMIZING NEEDLE-STICK PROBABILITY which issued Mar. 12, 1991, a safety device for hypodermic needles and the like is shown. The inventions shown hereinafter are improvements thereto by inventors including and/or working with Mr. Kuracina. In the interest of simplicity herein, the teachings of that patent are incorporated herein by reference and the discussion of the background art will be kept to a minimum.

A typical prior art hypodermic syringe 10 as shown in FIG. 1 includes a barrel 12 having a moving plunger 14 therein. A needle 16 having a sharp beveled tip 18 extends from the end opposite the end of the barrel 12 into which the plunger 14 is inserted. The needle 16 is covered by a removeable cap 20 for safety purposes. The problem to be solved and avoided is the accidental sticking of users of the syringe 10 by the tip 18 after the use where the tip 18 may carry body fluids containing agents of hepatitis B, AIDS, and the like. Accidental needle stick is a very common problem in the health care industry and besides the risk of serious illness or even death as a result thereof, the insurance industry spends over a billion dollars a year in the testing of individuals who have been subjected to post-use needle stick.

The 1979 patent of Alvarez proposed a retractable plastic protective sleeve over the needle. The Alvarez sleeve has an inner hub which fits around the base of the needle and an outer hub through which the tip of the needle passes. The inner and outer hubs are connected by curved slats. When the needle is to be inserted into the body of a patient, the force required to move the sleeve from its extended position to its retracted position can be depicted as a straight line beginning with very little required force to initiate movement. Thus, there is really no actually safety from a large variety of ways in which accidental needle stick takes place. Even if the sleeve fully extends after use, a slight blow against a user or observer in the area will cause the sleeve to retract and the tip to stick the unfortunate person.

With respect to the action of the basic protective sleeve of the above-referenced Kuracina patent by comparison, a high degree of force is required to move the protective sleeve from its extended position covering the tip. Moreover, a spring-biased locking collar is added over the protective sleeve which all but prevents the protective sleeve from moving from its extended position covering the tip. The collar must be moved from its locked position to a retracted, unlocked position before the unique deformation qualities of the sleeve take effect. After use, the locking collar springs back to its locked position. Thus, in virtually all "accidental" contact with the tip end of a hypodermic syringe, actual penetration by the tip should be prevented.

In a co-pending application entitled MEDICAL INJECTION DEVICES WITH SAFETY FEATURES filed on even date herewith, certain improvements to the Kuracina protective sleeve are disclosed. The inventions described hereinafter are protective hard covers intended to make the Kuracina protective sleeve even safer and more easy to use while also adapting it to various mounting configurations. Embodiments of the protective hard covers also have certain benefits when employed with conventional injection devices as well.

Other objects and benefits of the inventions disclosed herein will become apparent from the detailed description which follows hereinafter when taken in conjunction with the drawing figures which accompany it.

SUMMARY

The foregoing object has been achieved in a medical device having a needle carried by a base twistedly attached to the medical device, by the improvement for protectively capping the needle and providing ease of attachment and disattachment of the needle of the present invention comprising, the base having a plurality of radial longitudinal vanes; and, a hollow cover sized to fit over the needle and the plurality of radial longitudinal vanes, the cover having a closed end and an inwardly tapering open end into which the plurality of radial longitudinal vanes wedgedly fit to hold the base and the needle in the cover, the cover further having at least one inward projection contacting a side surface of one of the plurality of radial longitudinal vanes whereby a user can twist the base to attach and disattach the needle by twisting the cover.

Preferably, there is also a cap for closing the open end, the cap having a tapered inner portion shaped to wedgedly fit into the open end. Also, the preferred cap has a square shouldered outer portion abutting the tapered inner portion whereby the tapered inner portion can be twisted to remove it from the open end and the cap and the cover in combination are prevented from rolling off of flat surfaces.

For added security, the cap has a flat outer end surface opposite the tapered inner portion; the cover has a flat longitudinal outer sidewall aligned with a flat side of the square shouldered .outer portion; and, there is a safety strip of a frangible material adhesively attached to and over the flat outer end surface, the flat side of the square shouldered outer portion, and the flat longitudinal outer sidewall when the cover and cap contain a sterile needle whereby breaking of the safety strip prior to use indicates possible lack of sterility of the needle.

In any cover for a pre-filled medical device needle, an elastomeric material having the qualities of silicone rubber may be disposed within the closed end of the cover and in contact with a tip portion of a needle contained within the cover to seal the tip portion against leakage.

In any cover for a medical device needle, there may be a pierceable capsule carried by an outer surface of a closed end of the cover and containing a needle-sealing material therein whereby a needle contained within the cover can be sealed against further use by inserting a tip portion thereof through the capsule into the needle-sealing material. In one embodiment, the closed end of the cover has funnel-shaped sidewall means surrounding the pierceable capsule for guiding the tip portion of the needle into the pierceable capsule and the needle-sealing material contained therein. In another embodiment where the tip portion of the needle is disposed within a bell-shaped end of a protective sleeve, the pierceable capsule has a surface shaped to fit into the bell-shaped end whereby the tip portion of the needle can pierce the capsule without the protective sleeve being retracted.

Where the needle has a retractable protective sleeve disposed thereover with a bias spring and locking collar disposed over the retractable protective sleeve, including at least one vertical shoulder disposed inside the cover adjacent the open end holds the locking collar and the spring in a retracted position prior to use.

DESCRIPTION OF THE DRAWINGS

FIG. 1 is a simplified, partially cutaway drawing of a prior art hypodermic syringe with a removeable protective cap.

FIG. 2 is an end view of the needle-carrying inner hub of a protective sleeve assembly.

FIG. 3 is a cutaway drawing through the cap-carrying collar of a protective sleeve assembly.

FIG. 4 is an exploded view of the cap-carrying collar and the needle-carrying inner hub in an aligned configuration.

FIG. 7 is a side view of the protective hard cover of FIG. 5 with the end cap of FIG. 6 attached thereto.

FIG. 8 is an inner plan view of the end cap of FIG. 6.

FIG. 9 is a cutaway drawing through the body of the hard cover of FIG. 7 at IX.

FIG. 10 is a partial side view of the assembled hard cover and cap of FIG. 7 with the addition of a frangible safety strip.

FIG. 11 is a partially cutaway drawing of a hypodermic syringe employing a Kuracina type protective sleeve with a hard cover according to the present invention disposed thereover in an embodiment including a seal for sealing the end of the needle when the syringe is shipped pre-filled.

FIG. 12 is a partially cutaway drawing of a standard, unprotected hypodermic syringe with a hard cover according to the present invention disposed thereover in an embodiment including a seal for sealing the end of the needle when the syringe is shipped pre-filled.

FIG. 13 is a drawing of a portion of the hard cover of FIG. 11 depicting the addition of a compartment containing a sealing compound for rendering the needle and thereby the syringe unusable after use.

FIG. 14 is a drawing of a portion of the hard cover of FIG. 12 depicting the addition of a compartment containing a sealing compound for rendering the needle and thereby the syringe unusable after use.

DESCRIPTION OF THE PREFERRED EMBODIMENTS

Figure 5:
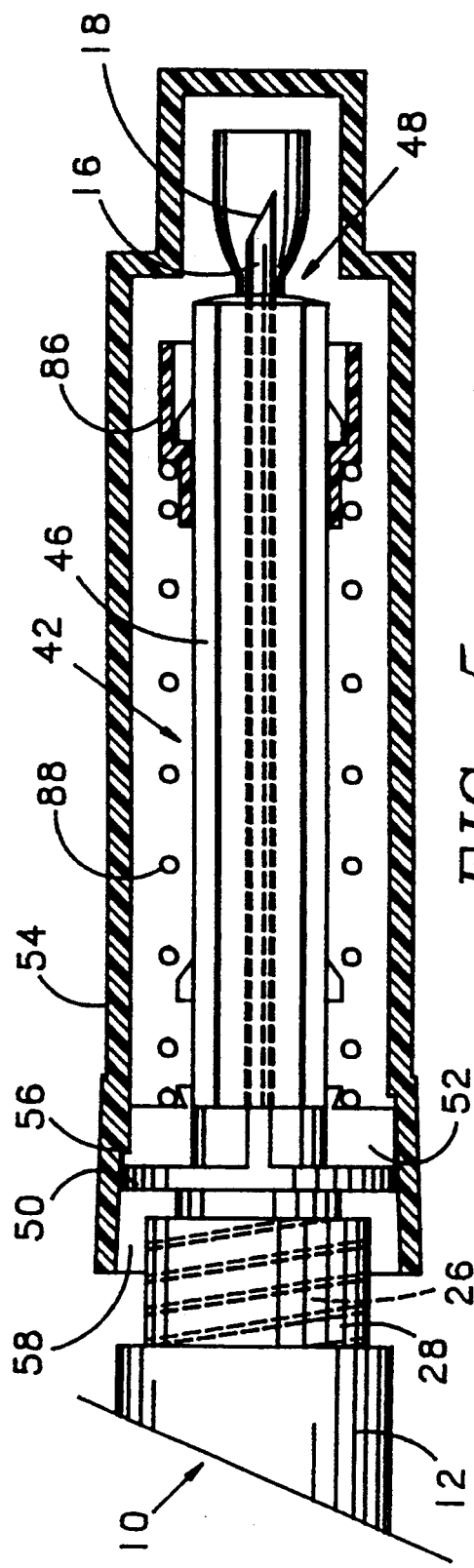
FIG. 5 is a partially cutaway view of a protective sleeve assembly with the addition of a preferred protective hard cover.
Figure 6:
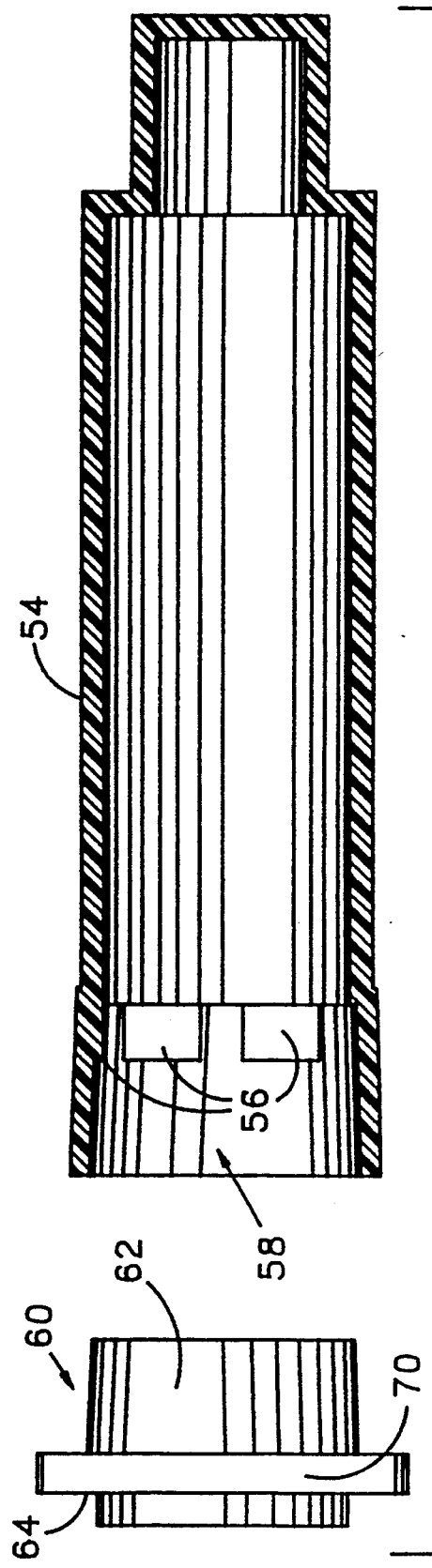
FIG. 6 is a partially cutaway view of the preferred protective hard cover of FIG. 5 with the associated end cap thereof.

Typically, in a prior art hypodermic syringe, the needle base is mounted over a cylindrical projection extending from the barrel. In an embodiment of copending application entitled MEDICAL INJECTION DEVICES WITH SAFETY FEATURES and as depicted in FIGS. 2-5 hereof, there is a needle/sleeve assembly 22 having a cylindrical hub assembly 24 which is threaded into internal threads 26 of a cylindrical hub 28 extending from the barrel 12 of the syringe 10. The hub assembly 24 comprises a cylindrical outer hub 30 which has a cylindrical inner hub 32 disposed therein. For alignment purposes, where desired, the inner hub 32 is retained by the projections 34 fitting into the bores 36. The inner hub 32 has ears 38 projecting outward therefrom which engage the threads 26 as the inner hub 32 is threaded into the outer hub 30. The inner hub 32 also concentrically holds the needle 16 at its base end in a bore 40 provided therefor. The outer hub 30 has the protective sleeve assembly 42 extending concentrically therefrom.

The protective sleeve assembly 42 comprises a cover-retaining hub 44 at the base end with the retracting slats 46 extending therefrom. The outer ends of the slats 46 are connected by an end cap 48. The cover-retaining hub 44 comprises a disk portion 50 having a plurality of radial vanes 52 extending forward therefrom. The vanes 52 can be employed to screw and unscrew the inner hub 32 with respect to the cylindrical hub 28 extending from the barrel 12 of the syringe 10.

The disk portion 50 and vanes 52 in combination can also support a hard cover 54 as shown ghosted in FIG. 3 and in a side, cutaway view in FIG. 5. The hard cover 54 can include inner projections 56 which fit between and engage the vanes 52 so that the hard cover 54 can be used to screw and unscrew the inner hub 32 with respect to the cylindrical hub 28 in a fully protected manner. The open end 58 of the hard cover 54 is also tapered inward to grip the disk portion 50 and vanes 52 as the hard cover 54 is pressed into place so as to prevent its inadvertent loss prior to intended removal for use. The complete needle/sleeve assembly 22 is shipped in the hard cover 54 and retained therein by the end cap 60. The end cap 60 has a tapered plug portion 62 sized and shaped to snuggly fit within the tapered open end 58 of the hard cover 54 and seal it and its contents from contamination. Preferably, the disk portion 50 and vanes 52 are tightly gripped by the open end 58 of the hard cover 54 as shipped so that the needle/sleeve assembly 22 can only be removed from the hard cover 54 by using the hard cover 54 to screw the needle/sleeve assembly 22 into a syringe 10 and then pulling the syringe 10 with the needle/sleeve assembly 22 attached and the hard cover 54 apart.

As best seen in FIG. 8, the end cap 60 has a square shoulder 64 adjacent the tapered plug portion 62. The square shoulder 64 serves several purposes. First, it provides a way of gripping the end cap 60 for removal by twisting and pulling without the necessity of breaking fingernails. Second, it prevents the hard cover 54 from inadvertently rolling off a surface upon which it has been placed. Third, and most important, it acts as part of a security sealing system. As shown in the cross-sectional drawing of FIG. 9, it is preferred that the hard cover 54 have a flattened outer surface 66 adjacent its open end 58. The flat outer end 68 of the end cap 60 in combination with one of the flat edges 70 of the shoulder 64 and the flattened outer surface 66 provide a continuous flat path bridging the joint 72 between the end cap 60 and the hard cover 54 over which a frangible security strip 74 can be placed at the time of original shipment. The security strip 74 is of a material and adhesively attached to this flat path using an adhesive of types well known in the art which result in the end cap 60 only being removeable from the hard cover 54 by breaking the security strip 74. Thus, if the security strip 74 is not intact at the time of use, the user knows that the hard cover 54 has been tampered with and that the contents may no longer be safe to use.

As the cost of manufacture of syringes goes down and the tendency towards one-use, disposable syringes goes up, there is a corresponding tendency to dispense injectable fluids in one-dose, disposable syringes. There are also additional advantages to such an approach which are not important to the next embodiment to be described. Suffice it to say that there is trend towards increased use of pre-filled syringes. In such case, there is a need to prevent leakage caused by jarring during shipping, dropping, and the like. As solution to this problem in the case of a syringe protected by a Kuracina type protective sleeve is depicted in FIG. 11. In this case, the inside of the closed end 76 of the hard cover 54 has a soft, silicone rubber finger 78 extending therefrom. The finger 78 is sized and shaped to fit within the preferred bell shape of the end cap 48. The tip 18 of the needle 16 embeds itself into the finger 78 and seals the needle 16 from leaking. Silicone rubber or a similar material is preferred for the finger 78 as it will not crumble and leave particles within or on the tip 18. FIG. 12 depicts a similar approach to sealing a conventional syringe 10 as in FIG. 1 not having a protective sleeve. In this case, the silicone rubber finger 78 is adhesively affixed to the inner end of the cap 20.

FIGS. 13 and 14 show provisions for sealing used needles to prevent reuse thereof which can be incorporated into hard covers or caps. In FIG. 13, the hard cover 54 has a pierceable capsule 80 attached to the outside of the closed end 76. As with the finger 78 of FIG. 11, the capsule 80 is sized and shaped to fit within the preferred bell shape of the end cap 48 and be pierced by the tip 18 of the needle 16. Thus, the protective sleeve does not have to be retracted to seal the needle 16. The capsule 80 contains a sealing material 82 which is forced into the open end of the needle 16 upon insertion and/or can be drawn into the needle 16 by withdrawing the plunger slightly. The sealing material 82 can be an adhesive material such as a silicone rubber sealant which is a fluid when kept from the air and then hardens to a rubber or harder consistency after exposure to the air. Being adhesives, such materials are virtually impossible to remove once they have set up. Within the small bore of a hypodermic needle, any attempt to remove the hardened sealing material 82 to render the needle usable once again would be more trouble than it was worth and almost assuredly result in failure. FIG. 14 shows a similar approach for the unprotected needle 16. In this case, the capsule 80 containing the sealing material 82 is contained within a guide cone 84 formed into the end of the cap 20 for safety purposes. Such an approach would not be desirable for use by health care workers dealing with others where there is a chance of exchange of body fluids during the needle sealing process. Such an approach could be employed with needles and other devices employed by diabetics, hemophiliacs, and the like, where it is a self-use situation and any accidental needle stick which takes place during the subsequent needle sealing process would be without consequence. At present, it is believed that most if not all of such equipment is merely discarded and is capable of being reused by others for other purposes, such as drug use, with the attendant risk of infection and contamination.

Figure 15:
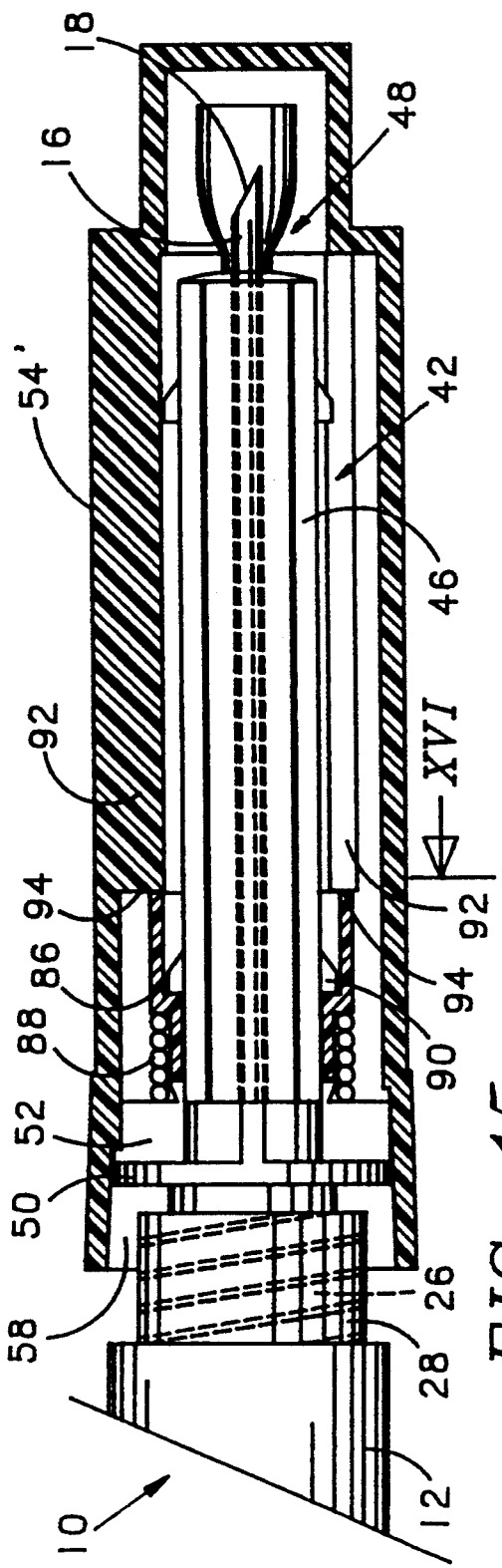
FIG. 15 is a partially cutaway drawing of a hypodermic syringe employing a Kuracina type protective sleeve with a hard cover according to the present invention disposed thereover in an embodiment including longitudinal vanes for retaining the locking collar in a retracted position prior to use.
Figure 16:
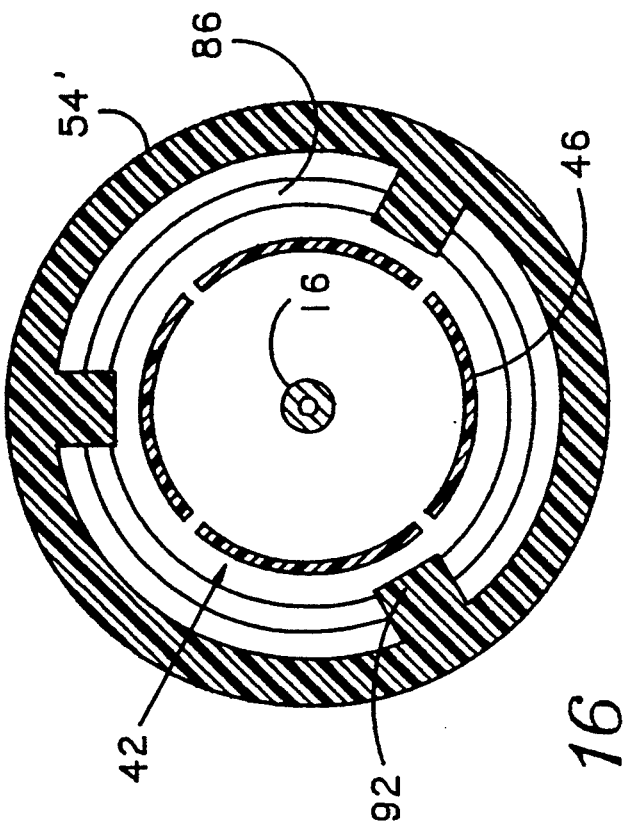
FIG. 16 is a cutaway view through the apparatus of FIG. 15 at XVI.

As mentioned in the above-referenced, co-pending application, there are instances where it may be desirable to ship a sleeve-protected device with the spring-biased locking collar 86 in its retracted position. The locking collar 86 then moves to its locked position after use. This is not a problem as it is only after use that the transfer of bodily fluids by means of accidental needlestick becomes a problem. A hard cap 54' for such instances is shown in FIGS. 15 and 16. The locking collar 86 is pulled back against the force of the spring 88 compressing the spring 88 and causing the locking collar 86 to be retained in its retracted position by the rear projections 90. To maintain the locking collar 86 in this position, prevent undue pressure on the various components, and prevent its accidental movement to its extended position (where in some embodiments it might lock against further use), the inside of the hard cover 54' is provided with longitudinal vanes 92 having bearing surfaces 94 which abut the end of the locking collar 86 and hold it in place. Note that it is the bearing surfaces 94 which are important and that the vanes 92 are included along the length of the hard cover 54' only because they are formed such during the injection molding process.

Wherefore, having thus described the present invention, what is claimed is:

1. A security package for a medical device needle carried by a base comprising:
   a) a hollow cover sized to fit over the needle and the base, said cover having a closed end and an inwardly tapering open end into which a mating portion of the base wedgedly fits to hold the base and the needle in said cover;
   b) a cap for closing said open end, said cap having a tapered inner portion shaped to wedgedly fit into said open end, said cap having a square shouldered outer portion abutting said tapered inner portion whereby said tapered inner portion can be twisted to remove it from said open end and said cap and said cover in combination are prevented from rolling off of flat surfaces, said cap further having a flat outer end surface opposite said tapered inner portion, said cover having a flat longitudinal outer sidewall aligned with a flat side of said square shouldered outer portion; and,
   c) a safety strip of a frangible material adhesively attached to and over said flat outer end surface, said flat side of said square shouldered outer portion, and said flat longitudinal outer sidewall whereby breaking of said safety strip prior to use indicates possible lack of sterility of the needle.

2. A medical device comprising:
   a) a needle carried by a base twistedly attached to the medical device, the needle having a retractable protective sleeve disposed thereover with a bias spring and locking collar disposed over said retractable protective sleeve and the base having a plurality of radial longitudinal vanes;
   b) a hollow cover sized to fit over the needle and sad plurality of radial longitudinal vanes for protectively capping the needle and providing ease of attachment and disattachment of the needle, said cover having a closed end and an inwardly tapering open end into which said plurality of radial longitudinal vanes wedgedly fit to hold the base and the needle in said cover, said cover further having at least one inward projection contacting a side surface of one of said plurality of radial longitudinal vanes whereby a user can twist the base to attach and disattach the needle by twisting said cover; and, c) a cap for closing said open end, said cap having a tapered inner portion shaped to wedgedly fit into said open end.

3. The medical device of claim 2 wherein:

said cap has a square shouldered outer portion abutting said tapered inner portion whereby said tapered inner portion can be twisted to remove it from said open end and said cap and said cover in combination are prevented from rolling off of flat surfaces.

4. The medical device of claim 3 wherein:

a) said cap has a flat outer end surface opposite said tapered inner portion; and, b) said cover has a flat longitudinal outer sidewall aligned with a flat side of said square shouldered outer portion; and additionally comprising, c) a safety strip of a frangible material adhesively attached to and over said flat outer end surface, said flat side of said square shouldered outer portion, and said flat longitudinal outer sidewall when said cover and cap contain a sterile needle whereby breaking of said safety strip prior to use indicates possible lack of sterility of the needle.

* * * * *